United States Patent [19]

Moini et al.

[11] Patent Number: 5,382,684

[45] Date of Patent: Jan. 17, 1995

[54] NITROGENOUS 1,3-SUBSTITUTED ADAMANTANES

[75] Inventors: Ahmad Moini, Lawrenceville, N.J.; Dong-Ming Shen, Langhorne, Pa.

[73] Assignee: Mobil Oil Corporation, Fairfax, Va.

[21] Appl. No.: 86,397

[22] Filed: Jul. 6, 1993

[51] Int. Cl.$^6$ .......................................... C07C 211/63
[52] U.S. Cl. .................... 564/281; 564/188; 564/454; 564/455
[58] Field of Search ................. 564/188, 281, 454, 455

[56] References Cited

U.S. PATENT DOCUMENTS

| | | | |
|---|---|---|---|
| 5,019,660 | 5/1991 | Chapman et al. | 585/22 |
| 5,053,434 | 10/1991 | Chapman | 521/52 |

FOREIGN PATENT DOCUMENTS

| | | |
|---|---|---|
| 451691 | 11/1974 | U.S.S.R. |
| 682507 | 8/1979 | U.S.S.R. |
| 1131871 | 12/1984 | U.S.S.R. |

OTHER PUBLICATIONS

Cashin et al, Chemical Abstracts, vol. 74 (1971) 141110a.
Inamoto et al, Chemical Abstracts, vol. 80 (1974) 59579a.
Chakrabarti et al, Chemical Abstracts, vol. 81 (1974) 99236p.
Aigami et al et al, Chemical Abstracts, vol. 83 (1975) 109072q.
Novakov et al, Chemical Abstracts, vol. 107 (1987) 190,397h.
Chakrabarti et al, Journal of Medicinal Chemistry, vol. 17, No. 6 (1974) pp. 602-609.

*Primary Examiner*—Richard L. Raymond
*Attorney, Agent, or Firm*—Alexander J. McKillop; Dennis P. Santini; Laurence P. Hobbes

[57] ABSTRACT

The invention is directed to nitrogenous 1,3-substituted adamantanes, their preparation and use in synthesis of inorganic porous solids. The nitrogenous 1,3-substituted adamantanes are compounds having the formula:

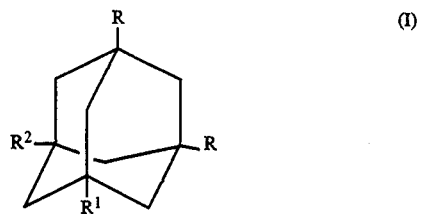

(I)

wherein R is a nitrogenous moiety selected from the group consisting of $-(CH_2)_{n-1}CONR'_2$, $-(CH_2)_nNR'_2$ and $-(CH_2)_nNR'_3{}^+A^-$, wherein R' is lower alkyl of 1 to 5 carbon atoms, $n=1$ to 5, $R^1$ and $R^2$ are selected from H and alkyl groups of 1 to 3 carbon atoms, and $A^-$ is an anion.

4 Claims, 1 Drawing Sheet

5,382,684

NITROGENOUS 1,3-SUBSTITUTED ADAMANTANES

FIELD OF THE INVENTION

This invention relates to nitrogenous 1,3-substituted adamantanes, their preparation and use in synthesis of inorganic porous solids.

BACKGROUND OF THE INVENTION

Porous inorganic solids have found great utility as catalysts and separations media for industrial application. The openness of their microstructure allows molecules access to the relatively large surface areas of these materials that enhance their catalytic and sorptive activity. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100–250 Angstrom particles of dense amorphous silica (*Kirk-Othmer Encyclopedia of Chemical Technology*, 3rd Edition, Vol. 20, John Wiley & Sons, New York, p. 766–781, 1982), with the porosity resulting from voids between the particles. Since there is no long range order in these materials, the pores tend to be distributed over a rather large range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions (K. Wefers and Chanakya Misra, "Oxides and Hydroxides of Aluminum" Technical Paper No. 19 Revised, Alcoa Research Laboratories, p. 54–59, 1987). Since, in the case of either material, there is no long range order controlling the sizes of pores in the material, the variability in pore size is typically quite high. The sizes of pores in these materials fall into a regime called the mesoporous range, which, for the purposes of this application, is from about 13 to 200 Angstroms.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g. $AlO_4$, in which the tetrahedra are crosslinked by the sharing of oxygen atoms whereby the ratio of the total Group IIIB element, e.g. aluminum, and Group IVB element, e.g. silicon, atoms to oxygen atoms is 1:2. The electrovalence of the tetrahedra containing the Group IIIB element, e.g. aluminum, is balanced by the inclusion in the crystal of a cation, for example, an alkali metal or an alkaline earth metal cation.

This can be expressed wherein the ratio of the Group IIIB element, e.g. aluminum, to the number of various cations, such as $Ca/2$, $Sr/2$, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865 and 4,104,294 describe crystalline silicate of varying alumina and metal content.

Aluminum phosphates are taught in U.S. Pat. Nos. 4,310,440 and 4,385,994, for example. These aluminum phosphate materials have essentially electroneutral lattices. U.S. Pat. No. 3,801,704 teaches an aluminum phosphate treated in a certain way to impart acidity.

An early reference to a hydrated aluminum phosphate which is crystalline until heated at about 110° C., at which point it becomes amorphous or transforms, is the "$H_1$" phase or hydrate of aluminum phosphate of F.d'Yvoire, Memoir Presented to the Chemical Society, No. 392, "Study of Aluminum Phosphate and Trivalent Iron", Jul. 6, 1961 (received), pp 1762–1776. This material, when crystalline, is identified by the JCPDS International Center for Diffraction Data card number 15–274. Once heated at about 110° C., however, the d'Yvoire material becomes amorphous or transforms to the aluminophosphate form of tridymite.

Compositions comprising crystals having a framework topology after heating at 110° C. or higher giving an X-ray diffraction pattern consistent with a material having pore windows formed by 18 tetrahedral members of about 12–13 Angstroms in diameter are taught in U.S. Pat. No. 4,880,611.

A naturally occurring, highly hydrated basic ferric oxyphosphate mineral, cacoxenite, is reported by Moore and Shen, Nature, Vol. 306, No. 5941, pp. 356–358 (1983) to have a framework structure containing very large channels with a calculated free pore diameter of 14.2 Angstroms. R. Szostak et al., *Zeolites: Facts, Figures, Future*, Elsevier Science Publishers B.V., 1989, present work showing cacoxenite as being very hydrophilic, i.e. adsorbing non-polar hydrocarbons only with great difficulty. Their work also shows that thermal treatment of cacoxenite causes an overall decline in X-ray peak intensity.

Silicoaluminophosphates of various structures are taught in U.S. Pat. No. 4,440,871. Aluminosilicates containing phosphorous, i.e. silicoaluminophosphates of particular structures are taught in U.S. Pat. Nos. 3,355,246 (i.e. ZK-21) and 3,791,964 (i.e. ZK-22). Other teachings of silicoaluminophosphates and their synthesis include U.S. Pat. Nos. 4,673,559 (two-phase synthesis method); 4,623,527 (MCM-10); 4,639,358 (MCM-1); 4,647,442 (MCM-2); 4,664,897 (MCM-4); 4,638,357 (MCM-5); and 4,632,811 (MCM-3).

A method for synthesizing crystalline metalloaluminophosphates is shown in U.S. Pat. No. 4,713,227, and an antimonophosphoaluminate and the method for its synthesis are taught in U.S. Pat. No. 4,619,818. U.S. Pat. No. 4,567,029 teaches metalloaluminophosphates, and titaniumaluminophosphate and the method for its synthesis are taught in U.S. Pat. No. 4,500,651.

The phosphorus-substituted zeolites of Canadian Patents 911,416; 911,417; and 911,418 are referred to as "aluminosilicophosphate" zeolites. Some of the phosphorus therein appears to be occluded, not structural.

U.S. Pat. No. 4,363,748 describes a combination of silica and aluminum-calcium-cerium phosphate as a low acid activity catalyst for oxidative dehydrogenation. Great Britain Patent 2,068,253 discloses a combination of silica and aluminum-calcium-tungsten phosphate as a low acid activity catalyst for oxidative dehydrogenation. U.S. Pat. No. 4,228,036 teaches an alumina-aluminum phosphate-silica matrix as an amorphous body to be mixed with zeolite for use as cracking catalyst. U.S. Pat. No. 3,213,035 teaches improving hardness of aluminosilicate catalysts by treatment with phosphoric acid. The catalysts are amorphous.

Other patents teaching aluminum phosphates include U.S. Pat. Nos. 4,365,095; 4,361,705; 4,222,896; 4,210,560; 4,179,358, 4,158,621; 4,071,471; 4,014,945; 3,904,550; and 3,697,550.

The precise crystalline microstructure of most zeolites manifests itself in a well-defined X-ray diffraction pattern that usually contains many sharp maxima and that serves to uniquely define the material. Similarly, the dimensions of pores in these materials are very regular, due to the precise repetition of the crystalline microstructure. All molecular sieves discovered to date have pore sizes in the microporous range, which is usually quoted as 2 to 20 Angstroms, with the largest reported being about 12 Angstroms.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, trititanates and perovskites. Another example of a non-water swellable layered material, which can be swollen with certain organic swelling agents, is a vacancy-containing titanometallate material, as described in U.S. Pat. No. 4,831,006.

Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials.

Other patents teaching pillaring of layered materials and the pillared products include U.S. Pat. Nos. 4,216,188; 4,248,739; 4,176,090; and 4,367,163; and European Patent Application 205,711.

The X-ray diffraction patterns of pillared layered materials can vary considerably, depending on the degree that swelling and pillaring disrupt the otherwise usually well-ordered layered microstructure. The regularity of the microstructure in some pillared layered materials is so badly disrupted that only one peak in the low angle region on the X-ray diffraction pattern is observed, as a d-spacing corresponding to the interlayer repeat in the pillared material. Less disrupted materials may show several peaks in this region that are generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

The synthetic porous inorganic materials are generally produced from a reaction mixture (or "gel") which contains the precursors of the synthetic material. Because the necessary seed crystals may be unavailable (particularly when the porous inorganic material is new and has not previously been synthesized) it would be desirable to provide a synthesis method which generates a selected porous inorganic material from a particular reaction mixture containing no nucleating seeds.

The reaction mixture for a particular porous inorganic material may also contain an organic directing agent or templating agent. The terms "templating agent" and "directing agent" are both used to describe compounds (usually organics) added to the reaction mixture to promote formation of the desired porous inorganic solid.

Bulky organic bases which are favored as directing agents include cetyltrimetylammonium (CTMA), myristyltrimethylammonium ($C_{14}$TMA), decyltrimethylammonium, cetyltrimethylphosphonium, octadecyltrimethylphosphonium, benzyltrimethylammonium, cetylpyridinium, dodecyltrimethylammonium, and dimethyldidodecylammonium, merely to name a few. The templating action of various organic entities is also discussed in A. Dyer *An Introduction to Zeolite Molecular Sieves* 60 (1988), as well as in B. M. Lok et al., The Role of Organic Molecules in Molecular Sieve Synthesis 3 *Zeolites* 282 (1983), which are incorporated by reference as if set forth at length herein. These materials are costly, and usually account for most of the materials-related expense in the synthesis of zeolites.

Adamantane, tricyclo-[3.3.1.1$^{3,7}$]decane, is a polycyclic alkane with the structure of three fused cyclohexane rings. The ten carbon atoms which define the framework structure of adamantane are arranged in an essentially strainless manner. Four of these carbon atoms, the bridgehead carbons, are tetrahedrally disposed about the center of the molecule. The other six (methylene carbons) are octahedrally disposed. U.S. Pat. Nos. 5,019,660 to Chapman and Whitehurst and 5,053,434 to Chapman teach diamondoid compounds which bond through the methylene positions of various diamondoid compounds, including adamantane. For a survey of the chemistry of diamondoid molecules, see *Adamantane, The Chemistry of Diamond Molecules*, Raymond C. Fort, Marcel Dekker, New York, 1976.

Adamantane has been found to be a useful building block in the synthesis of a broad range of organic compounds.

SUMMARY OF THE INVENTION

The present invention is directed to nitrogenous 1,3-substituted adamantanes, their preparation and use in synthesis of inorganic porous solids. The nitrogenous 1,3-substituted adamantanes are compounds having the formula:

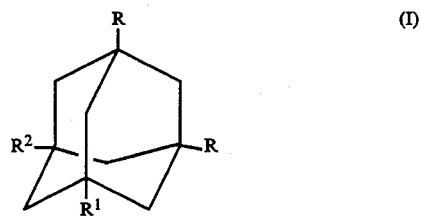

(I)

wherein R is a nitrogenous moiety selected from the group consisting of —(CH$_2$)$_{n-1}$ CONR'$_2$, —(CH$_2$)$_n$NR'$_2$, and —(CH$_2$)$_n$NR'$_3$+A$^-$, wherein R' is lower alkyl of 1 to 5 carbon atoms, n is an integer from 1 to 5, and R$^1$ and R$^2$ are each selected from the group consisting of H and lower alkyls having 1 to 3 carbon atoms, and A$^-$ is an anion. Such materials can be employed in a method for synthesis of a porous inorganic solid comprising forming a reaction mixture containing water, an alumina source, a silica source, an alkali metal oxide source, and a quaternary ammonium salt having the formula

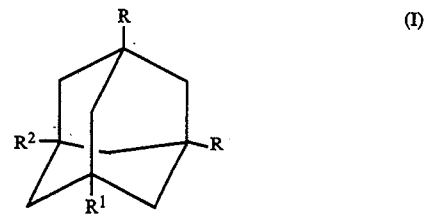

(I)

wherein R is a nitrogenous moiety selected from the group consisting of —(CH$_2$)$_n$NR'$_2$ and —(CH$_2$)$_n$NR'$_3$+A$^-$, wherein R' is lower alkyl of 1 to 5 carbon atoms, n is an integer from 1 to 5, R$^1$ and R$^2$ are selected from H and lower alkyls with 1 to 3 carbon atoms, and A$^-$ is an anion which is not detrimental to the formation of the porous inorganic solid. Reaction temperature may range from below ambient to about 400° C., and temperatures of from about 120° to about 180° C. are preferred for crystallization of the zeolite mordenite.

In one embodiment, the reaction mixture is further characterized by the following approximate molar ratios of oxides, where Z represents a quaternary ammonium salt of the present invention and M+ represents an alkali ion.

| | |
|---|---|
| SiO$_2$/Al$_2$O$_3$: | 15 to ∞ |
| OH$^-$/SiO$_2$: | 0.05 to 1.0 |
| H$_2$O/SiO$_2$: | 10 to 150 |
| Z/SiO$_2$: | 0.02 to 0.80 |
| M+/SiO$_2$: | 0.05 to 1.0 |

The synthesis method of the invention functions with or without added nucleating seeds. In a preferred embodiment, the reaction mixture contains no nucleating seeds. The porous inorganic solid synthesized in accordance with the invention is preferably a crystalline microporous material.

The invention further includes a method for the preparation of the compositions of the present invention from adamantane-1,3-bis(carboxylic acid), including adamantane-1,3-bis(N,N-dialkylcarboxamide), adamantane-1,3-bis(N,N-dialkylmethanamine and adamantane-1,3-bis(N,N,N-trialkylmethanaminium) compounds.

The new templates and the specific conditions using these templates as disclosed herein facilitate the crystallization of mordenite as well as other zeolites and layered silicates. Further, the samples synthesized in accordance with the present invention showed useful catalytic activity as evidenced by observed high Alpha values.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0,016 sec$^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

The synthesis process of the invention hydrothermally produces mordenite crystals at a $SiO_2/Al_2O_3$ feed ratio of 40 to 120, and at temperatures between 150° and 190° C.

In accordance with the present invention, mordenite can be synthesized hydrothermally using the above adamantane-containing diquaternary ammonium halides as templates. The preferred aluminum source is $NaAlO_2$, while the preferred silicon source is $SiO_2$ sol (30% $SiO_2$ in $H_2O$), which is commercially available as Catalog No. SX01401-1 from EM Science, Inc.

Mordenite is a large pore zeolite comprising intersecting 12 ring and 8 ring channels as described in "Atlas of Zeolite Structure Types, W. M. Meier and D. H. Olson, 2nd Revised Ed., 1987, Butterworths. This zeolite is further described in U.S. Pat. No. 4,503,023 to Breck et al., incorporated herein by reference.

BRIEF DESCRIPTION OF THE DRAWING

The figure represents an X-ray diffraction pattern of the product of Example 4.

Embodiments

Synthesis of the Directing Agent

Figure 1:
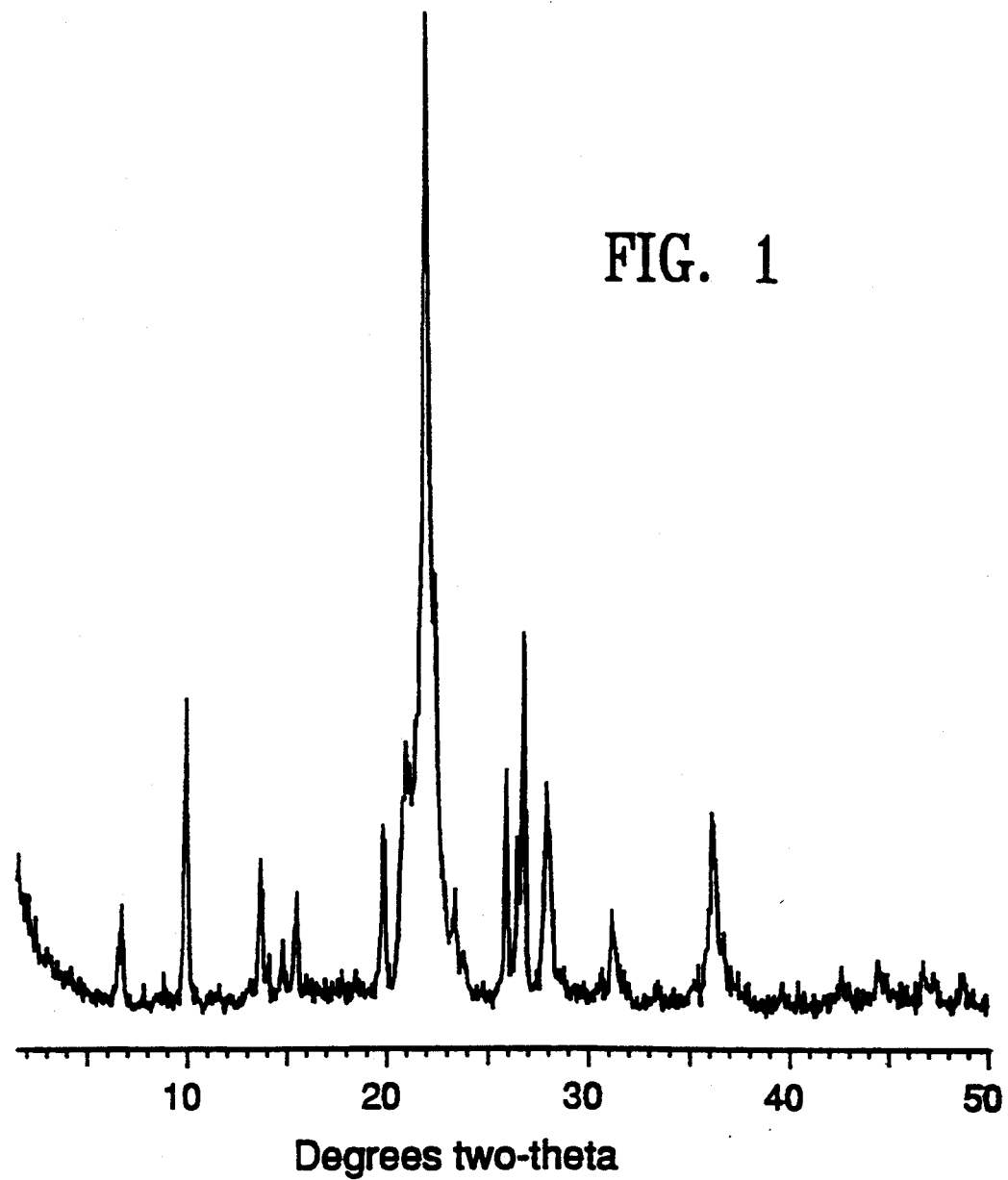

The directing agent of the present invention may suitably be synthesized in accordance with the following general procedure which includes the sequential steps of: (1) acid chloride formation between adamantane 1,3-bis(carboxylic acid) and thionyl chloride, (2) formation of adamantane-1,3-bis(N,N-dialkyl carboxamide) by reaction of the dicarboxylic acid with dialkyl amine, (3) hydrogenation of the carboxamide to adamantane-1,3-bis(N,N-dialkylmethanamine) by reduction with HAl(i-Bu)$_2$ or LiAlH$_4$ and hydrolysis, and (4) quaternization with alkyl halide. These nitrogen-containing adamantane compounds are useful as nucleating agents for syntheses of zeolites and other porous catalysts, as well as for pharmeceutical applications as antivirals.

The following Examples illustrate the synthesis of diquaternary ammonium compounds useful as directing agents in the method of the present invention:

EXAMPLE 1

Preparation of adamantane-1,3-bis(N,N-dimethyl carboxamide (II)

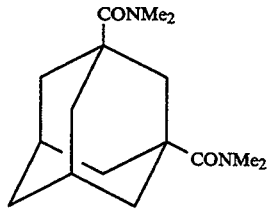

(II)

a) Adamantane-1,3-bis(carbonyl chloride):

205.70 g (0.917 mol) adamantane-1,3-bis(carboxylic acid) were refluxed with 1400 g SOCl$_2$ until the acid dissolved. Excess SOCl$_2$ was distilled off under partial vacuum. Care was taken not to let the product be heated over about 90° C. during this process to avoid decomposition. A gray solid (239.86 g) was obtained at the end and was used in the next step without further purification. It was distilled using a Kugelrohr set-up at 80° C. (pot) and about 1 mm-Hg vacuum to give a colorless solid. $^{13}$C-NMR (CDCl$_3$, 15 MHz): 170.09, 51.38, 40.08, 37.99, 34.77, 27.86;

b) Adamantane-1,3-bis(N,N-dimethyl carboxamine) (II)

Adamantane-1,3-bis(carbonyl chloride) prepared above was dissolved in 3.5 l ether in a 5 l 4-necked flask fitted with a mechanical stirrer, a stopper, an addition funnel, and a reflux condenser having a dry-ice cooled condenser at the top. About 205 g anhydrous dimethyl amine were transferred from a chilled cylinder to the funnel containing 500 ml ether. This solution was added to the flask with stirring over 3 hours with heat from the reaction keeping the reaction mixture at reflux much of the time. A white precipitate was formed during the addition after which a mixture of 50 g Me$_2$NH and 100 g ether was added and the mixture stirred overnight. The reaction mixture was filtered to collect the solid which was washed with ether. Yellowish solid recovered from this ether solution was boiled with 300 ml ether, cooled, and filtered to give about 42.0 g yellowish solid (Part 1). The filtered solid (direct from the reaction mixture) was further washed with 4×250 mL water (Part 2) and dried to give 128.76 g white solid, m.p. 139.9°-140.0° C. Its NMR showed that it was pure bis-amide: $^{13}$C-NMR/DEPT (CDCl$_3$, 90 MHz): 176.11 (C=O), 42.38 (s), 39.60 (1 CH$_2$), 38.67 (CH$_3$), 38.00 (4 CH$_2$), 35.73 (1 CH$_2$), 28.76 (CH). The aqueous wash (Part 2) was cooled with ice and 49.32 g of NaOH pellets were added in small portions with stirring. Some crystals were formed during this process. The solution part of the mixture was concentrated to 700 ml, combined with Part 1 of the crude product and the mixture recrystallized. The resulting crystals were collected, washed with 2×50 ml water, and dried to give 68.2 g slightly yellowish crystals of bis-amide, m.p. 139.5°-140.1° C. Its $^{13}$C-NMR was the same as the above. $^1$H-NMR (CDCl$_3$, 360 MHz): 3.07 (s,12H), 2.26 (br s, CH$_2$), 2.21-2.19 (br m, 2 CH), 2.01 and 1.99 (AB d), 1.69 (t, 2.9 Hz, CH$_2$). The mother liquor and aqueous wash solution were concentrated to give a lightly yellowish solid, washed with 2×25 ml water, and dried to give 58.94 g solid. This product was only partially soluble in CDCl$_3$, but the soluble part was pure product based on NMR and GC analyses. The insoluble part was NaCl. This mixture was extracted in a Soxhlet extractor with ether to give 12.21 g white solid bis-amide (II). The combined weight of the bis-amide was 209.2 g, 82%. The slightly lower than expected yield of bis-amide was largely due to a spill during the reaction.

EXAMPLE 2

Adamantane-1,3-bis(N,N-dimethylmethanamine) (III)

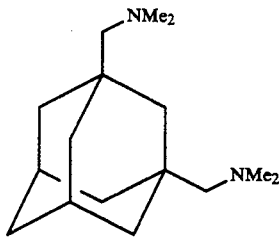

68.2 g of bis-amide were suspended in 1.4 l of anhydrous ether in a 5 l 4-neck flask fitted with a reflux condenser, an addition funnel, a thermometer, and a mechanical stirrer. The flask was cooled with an ice-/water bath and 400 ml 1.0M LiAlH$_4$ ether solution were added to the flask from the funnel with stirring over 4.5 hours forming a white suspension. The reaction mixture was stirred for 12 hours, then heated to reflux for 2 hours. GC analysis showed no starting material remained. 20 ml of saturated Na$_2$SO$_4$ solution were added dropwise with stirring to the reaction mixture to partially hydrolyze the reaction mixture. The resulting reaction mixture was filtered by suction, taking care not to draw too much air through the filter cake to avoid exothermic oxidation of the residual LiAlH$_4$ inside. The ether solution was dried over anhydrous Na$_2$SO$_4$ and the ether removed on a rotary evaporator to give 49.30 g colorless liquid (80%). GC analysis showed it was 99.6% diamine and 0.4% higher boiling material (triamine). Almost no adamantane-1-(N,N-dimethylmethanamine)-3-methanol was present. $^{13}$C-NMR (CDCl$_3$, 90 MHz) of diamine: 72.97 (2 CH$_2$), 59.23 (4 CH$_3$), 44.51 (1 CH$_2$), 40.66 (4 CH$_2$), 36.70 1 CH$_2$), 35.34 (2 C), 28.78 (2 CH). $^1$H-NMR (CDCl$_3$, 360 MHz): 2.27 (2,12H), 2.02 (br s, 2 CH), 1.97 (s, 2 CH$_2$), 1.59 (br s, 1 CH$_2$), 1.48 and 1.43 (AB d, 11.7 Hz, 4 CH$_2$), 1.26 (br s, 1 CH$_2$). Elemental analysis found: C 76.35, H 12.50; calcd.: C 76.74, H 12.07. The higher boiling impurities were removed by vacuum distillation, b.p. 86°~87° C./0.15 mm-Hg. Side-products such as adamantane-1-(N,N-dimethylmethanamine)-3-methanol present after the work-up were removed by vacuum-distilling the crude product with an appropriate amount of LiAlH$_4$. The alcohol products were converted to salts and were left in the pot while the bis-amine (III) was distilled.

EXAMPLE 3

Adamantane-1,3-bis(N,N,N-trimethylmethanaminium iodide) (IV)

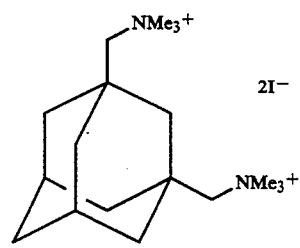

80.71 g (0.322 mol) adamantane-1,3-bis(N,N-dimethylmethanamine) (III) from Example 2 were dissolved in 480 ml absolute ethanol in an 1 l 4-neck round-bottom flask fitted with a reflux condenser, an addition funnel, a mechanical stirrer, and a stopper. The mixture was heated to reflux under N$_2$. 148.0 g MeI (1.04 mol) were added from the funnel to the flask over 3 hours with stirring. After about a third of the MeI was added, a white precipitate began to form in the flask. Heating was continued for an additional 12 hours. After cooling, the white solid was collected to give 170.04 g white solid (99%) as the ammonium salt (IV), m.p. 281.5°–287.6° C. (decompose, sublime). NMR showed that it was pure product. $^{13}$C-NMR (CDCl$_3$, 90 MHz): 79.81 (t, 2.2 Hz, 2 CH$_2$), 58.71 (t, 4.0 Hz, 4 CH$_3$), 47.35 (1 CH$_2$), 42.10 (4 CH$_2$), 38.81 (2 C), 37.02 (1 CH$_2$), 30.55 (2CH). $^1$H-NMR (CDCl$_3$, 360 MHz): 4.72 (s,4H), 3.27 (3, 12H), 2.23 (br s, 2H), 1.91 and 1.83 (AB d, 11.9 Hz, 8H), 1.83 (br s, 2H), 1.72 (br s, 2H). The initial product can be recrystallized in water to give colorless crystals of the salt (IV). The amount of water (ml) used, dry product obtained (g), and the melting points of the various crops of products were 360°, 125.20°, 281.2°–284.6° C. (decompose, sublime); 50°, 33.16°, 281.2°–284.6° C. (decompose, sublime); and 10°, 8.06°, 281.2°–284.6° C. (decompose, sublime). The recrystallized product totaled 166.44 g (97%).

EXAMPLE

Mordenite

Colloidal silica sol (30% SiO$_2$), sodium aluminate, NaOH (50%), the iodide salt of the di-quat (IV), and water were mixed. The amounts used corresponded to the following molar ratios:

| Si/Al2 | H2O/Si | OH−/Si | Na+/Si | Z/Si |
| --- | --- | --- | --- | --- |
| 90 | 60 | 0.26 | 0.28 | 0.10 |

The hydrogel was placed in a 300 ml Teflon ®-lined stainless steel autoclave and heated at 180° C., with stirring, for 6 days. The final product was filtered and washed with H$_2$O. The X-ray diffraction pattern for the product set out in the Figure showed the presence of the zeolite mordenite and the dense SiO$_2$ phase cristobalite.

Changes and modifications in the specifically described embodiments can be carried out without departing from the scope of the invention which is intended to be limited only by the scope of the appended claims.

What is claimed is:

1. A nitrogenous 1,3-substituted adamantane compound having the formula:

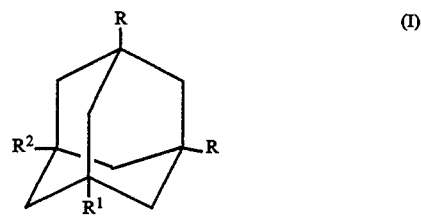

wherein R is —(CH$_2$)$_n$NR'$_{-3}$+A—, wherein R' is lower alkyl of 1 to 5 carbon atoms, A— is an anion, n is an integer from 1 to 5, and R$^1$ and R$^2$ are each selected from H and alkyl groups of 1 to 3 carbon atoms.

2. The compound of claim 1 wherein R' is methyl.

3. The compound of claim 1 wherien R' is ethyl.

4. The compound of claim 1 wherein R' is methyl, and A is halogen.

* * * * *